(12) United States Patent
Mitchell et al.

(10) Patent No.: US 10,194,660 B2
(45) Date of Patent: Feb. 5, 2019

(54) HERBICIDAL COMPOUNDS

(71) Applicant: Syngenta Participations AG, Basel (CH)

(72) Inventors: Glynn Mitchell, Bracknell Berkshire (GB); Nicholas Phillip Mulholland, Bracknell Berkshire (GB); Yunas Bhonoah, Bracknell Berkshire (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/735,843

(22) PCT Filed: Jun. 10, 2016

(86) PCT No.: PCT/EP2016/063273
§ 371 (c)(1),
(2) Date: Dec. 12, 2017

(87) PCT Pub. No.: WO2016/198585
PCT Pub. Date: Dec. 15, 2016

(65) Prior Publication Data
US 2018/0177190 A1    Jun. 28, 2018

(30) Foreign Application Priority Data
Jun. 12, 2015 (GB) .................... 1510254.4

(51) Int. Cl.
| *A01N 43/80* | (2006.01) |
| *A01N 43/653* | (2006.01) |
| *A01N 43/713* | (2006.01) |
| *C07D 403/12* | (2006.01) |
| *C07D 403/14* | (2006.01) |
| *C07D 413/14* | (2006.01) |

(52) U.S. Cl.
CPC ........ *A01N 43/713* (2013.01); *A01N 43/653* (2013.01); *A01N 43/80* (2013.01); *C07D 403/12* (2013.01); *C07D 403/14* (2013.01); *C07D 413/14* (2013.01)

(58) Field of Classification Search
CPC ... C07D 403/12; C07D 403/14; C07D 413/14
See application file for complete search history.

(56) References Cited

U.S. PATENT DOCUMENTS

| 4,251,531 A * | 2/1981 | Doria ................... C07D 239/90 514/266.23 |
| 2015/0216171 A1* | 8/2015 | Ahrens ................ C07D 413/14 504/105 |

FOREIGN PATENT DOCUMENTS

| DE | 2008009609 A1 | 8/2009 |
| WO | 2013/076315 A2 | 5/2013 |
| WO | 2013/076316 A1 | 5/2013 |
| WO | 2013144231 A1 | 10/2013 |
| WO | 2014037342 A1 | 3/2014 |
| WO | 2015/007564 A1 | 1/2015 |

OTHER PUBLICATIONS

GB Search report, Application No. 1510254.4, dated Mar. 11, 2016.
International Search Report, Application No. PCT/EP2016/063273 dated Jul. 13, 2016.

* cited by examiner

*Primary Examiner* — John Pak
(74) *Attorney, Agent, or Firm* — Toni-Junell Herbert; Dinsmore & Shohl LLP

(57) ABSTRACT

The present invention relates to compounds of Formula (I), or an agronomically acceptable salt of said compounds wherein $A^{1a}$, $A^{1b}$, $R^1$, $R^2$, $R^3$ and $R^4$ and $R^5$ are as defined herein. The invention further relates to herbicidal compositions which comprise a compound of Formula (I), and to their use for controlling weeds, in particular in crops of useful plants.

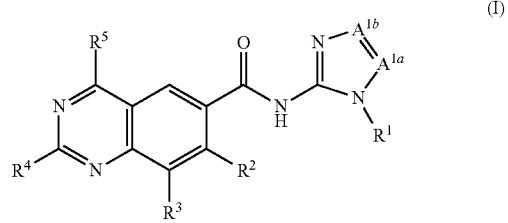

(I)

13 Claims, No Drawings

HERBICIDAL COMPOUNDS

RELATED APPLICATION INFORMATION

This application is a 371 of International Application No. PCT/EP2016/063273 filed Jun. 10, 2016, which claims priority to GB Application No. 1510254.4 filed Jun. 12, 2015, the contents of which are incorporated herein by reference herein.

The present invention relates to novel herbicidal compounds, to processes for their preparation, to herbicidal compositions which comprise the novel derivatives, and to their use for controlling weeds, in particular in crops of useful plants, or for inhibiting plant growth.

Herbicidal N-(tetrazol-5-yl)- and N-(triazol-5-yl)-arylcarboxamides are disclosed in, for example, WO 2012/028579, WO 2013/092834 and WO 2014/037342. The present invention provides further herbicidal derivatives. Thus, according to the present invention there is provided a compound of Formula (I):

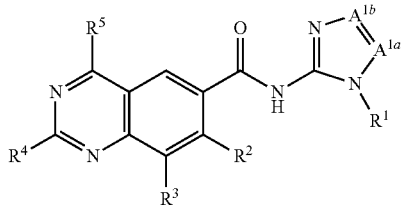

or an agronomically acceptable salt thereof,
wherein:—
$A^{1a}$ and $A^{1b}$ are independently selected from CH and N, wherein $A^{1a}$ and $A^{1b}$ are not both CH;
$R^1$ is selected from the group consisting of $C_1$-$C_6$alkyl-, $C_1$-$C_6$alkoxy$C_1$-$C_3$-alkyl-, $C_1$-$C_6$haloalkoxy$C_1$-$C_3$alkyl-, $C_1$-$C_6$haloalkyl-, $C_2$-$C_6$alkenyl-, $C_2$-$C_6$haloalkenyl-, $C_2$-$C_6$alkynyl-, $C_2$-$C_6$haloalkynyl-, heteroaryl- (e.g pyridyl), ($C_3$-$C_7$)cycloalkyl-, heterocyclyl- (e.g thietanyl, tetrahydropyranyl) and phenyl-, wherein the heteroaryl-, ($C_3$-$C_7$)cycloalkyl-, heterocyclyl- and phenyl- are optionally substituted by one or more substituents selected from the group consisting of halogen, nitro, cyano, $C_1$-$C_6$alkyl-, $C_1$-$C_6$haloalkyl-; $C_3$-$C_6$cycloalkyl-, $C_1$-$C_6$alkylS(O)p-, $C_1$-$C_3$alkoxy- and $C_1$-$C_6$alkoxy$C_1$-$C_4$alkyl-;
$R^2$ is selected form the group consisting of $C_1$-$C_6$alkyl-, $C_1$-$C_6$alkoxy-, $C_1$-$C_6$ haloalkyl-, $C_1$-$C_6$haloalkoxy-, $C_1$-$C_6$alkoxy$C_1$-$C_6$alkyl-, $C_1$-$C_3$alkoxy$C_2$-$C_3$alkoxy$C_1$-$C_3$alkyl-, $C_1$-$C_3$alkoxy$C_1$-$C_3$haloalkyl-, $C_1$-$C_3$-alkoxy-$C_1$-$C_3$-alkoxy-$C_2$-$C_3$-haloalkyl-, halogen, cyano, nitro, $C_1$-$C_6$alkyl-S(O)p-, $C_1$-$C_6$haloalkyl-S(O)$_p$—, $C_4$-$C_6$-oxasubstituted-cycloalkoxy-$C_1$-$C_3$-alkyl-, $C_4$-$C_6$-oxasubstituted-cycloalkoxy-$C_1$-$C_3$-haloalkyl-, ($C_1$-$C_3$-alkanesulfonyl-$C_1$-$C_3$ alkylamino)-$C_1$-$C_3$alkyl- and ($C_1$-$C_3$alkanesulfonyl-$C_3$-$C_4$cycloalkylamino)-$C_1$-$C_3$ alkyl-;
$R^3$ is aryl or a 5 or 6-membered heteroaryl, the heteroaryl containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxy$C_1$-$C_3$alkyl-, $C_1$-$C_6$alkoxy$C_1$-$C_3$alkoxy-, $C_1$-$C_6$haloalkoxy-, $C_1$-$C_6$alkyl-S(O)p-, —NR$^{6a}$R$^{6b}$, cyano and nitro;
$R^4$ is selected from the group consisting of hydrogen, halogen, $C_1$-$C_6$-alkyl-, $C_3$-$C_6$cycloalkyl-, $C_1$-$C_6$-alkoxy-$C_1$-$C_3$-alkyl-, $C_1$-$C_6$-haloalkoxy-$C_1$-$C_3$-alkyl-, $C_1$-$C_6$-haloalkyl-, $C_2$-$C_6$-alkenyl-, $C_2$-$C_6$-haloalkenyl-, $C_2$-$C_6$-alkynyl-, $C_2$-$C_6$-haloalkynyl, $C_1$-$C_6$alkoxy-, $C_1$-$C_6$alkyl-S(O)p- and NR$^{6a}$R$^{6b}$;
$R^5$ is selected from the group consisting of hydrogen, halogen and $C_1$-$C_6$-alkyl-;
R$^{6a}$ and R$^{6b}$ are independently selected from the group consisting of hydrogen and $C_1$-$C_6$alkyl or together form a $C_4$-$C_5$ alkylene chain; and
p=0, 1 or 2.

$C_1$-$C_6$alkyl- includes, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

$C_2$-$C_6$alkenyl- includes, for example, —CH=$CH_2$ (vinyl) and —$CH_2$—CH=$CH_2$ (allyl).

$C_2$-$C_6$alkynyl- includes, for example, —C≡CH (ethynyl) and —$CH_2$—C≡CH (propargyl).

$C_3$-$C_6$cycloalkyl- includes cyclopropyl (c-propyl (c-Pr)), cyclobutyl (c-butyl (c-Bu)), cyclopentyl (c-pentyl) and cyclohexyl (c-hexyl).

Halogen (or halo) encompasses fluorine, chlorine, bromine or iodine. The same correspondingly applies to halogen in the context of other definitions, such as haloalkyl or halophenyl.

$C_1$-$C_6$haloalkyl- includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

$C_1$-$C_6$alkoxy- includes, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom may be joined to form a spiro group. Thus, the methyl groups present in two methoxy substituents may be joined to form a spiro 1,3 dioxolane substituent, for example. Such a possibility is within the scope of the present invention.

$C_1$-$C_6$haloalkoxy- includes, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkoxy$C_1$-$C_6$alkyl- includes, for example, methoxymethyl, methoxyethyl, ethoxymethyl, ethoxyethyl, n-propoxymethyl, n-propoxyethyl, isopropoxymethyl or isopropoxyethyl.

$C_1$-$C_6$haloalkoxy-$C_1$-$C_3$alkyl- includes, for example, 2,2,2-trifluoro-ethoxymethyl-.

$C_1$-$C_6$alkoxy$C_2$-$C_3$alkoxy$C_1$-$C_3$alkyl- includes, for example, methoxyethoxymethyl-.

$C_1$-$C_6$alkyl-S— (alkylthio) includes, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) includes, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-$S(O)_2$— (alkylsulfonyl) includes, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino (e.g —$NR^{6a}R^{6b}$) includes, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

In one embodiment of the present invention is a compound of Formula (I) wherein Ala is CH and $A^{1b}$ is N. In another embodiment, $A^{1a}$ is N and $A^{1b}$ is CH. In a particularly preferred embodiment, both $A^{1a}$ and $A^{1b}$ are N.

In another embodiment, $R^1$ is selected from the group consisting of methyl, ethyl and n-propyl.

In another preferred embodiment, $R^2$ is selected form the group consisting of $C_1$-$C_6$alkyl- (preferably methyl), $C_1$-$C_6$alkoxy- (preferably methoxy-), $C_1$-$C_6$ haloalkyl- (preferably trifluoromethyl-), halogen (preferably chlorine) and $C_1$-$C_6$alkyl-S(O)p- (preferably —$SO_2$-methyl). In a particularly preferred embodiment, $R^2$ is $C_1$-$C_6$alkyl- (preferably methyl) or $C_1$-$C_6$haloalkyl- (preferably trifluoromethyl-). In a particularly preferred embodiment, $R^2$ is methyl, chlorine or trifluoromethyl.

In another embodiment, $R^3$ is an aryl or heteroaryl selected from the group consisting of phenyl, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl all of which may be optionally substituted as described herein. In a preferred embodiment, $R^3$ is selected from the group consisting of phenyl, thiophenyl, isoxazolyl, pyrimidinyl and pyridyl all of which may be optionally substituted as described herein. In an even more preferred embodiment, $R^3$ is selected from the group consisting of phenyl, isoxazolyl and pyrimidinyl all of which may be optionally substituted as described herein (e.g 3,5-dimethylisoxazol-4-yl or 2-MeO-pyrimidin-5-yl)). In a particularly preferred embodiment, $R^3$ is phenyl optionally substituted by one or more substituents selected from the group consisting of halogen (especially fluorine and/or chlorine), $C_1$-$C_6$alkyl- (especially methyl), $C_1$-$C_6$haloalkyl- (especially trifluoromethyl), $C_1$-$C_6$alkoxy- (especially methoxy-), $C_1$-$C_6$haloalkoxy- (especially trifluoromethyl-oxy-, $C_1$-$C_6$alkyl-S(O)p- (especially —$SO_2$-methyl), cyano and nitro.

In another preferred embodiment $R^4$ is selected from the group consisting of hydrogen, $C_1$-$C_6$alkyl- (e.g methyl, i-propyl), $C_3$-$C_6$cycloalkyl- (e.g c-propyl) and $C_1$-$C_6$haloalkyl- (e.g trifluoromethyl). In a particularly preferred embodiment, $R^4$ is hydrogen, methyl or trifluoromethyl.

In another preferred embodiment, $R^5$ is selected from the group consisting of hydrogen, fluorine, chlorine and methyl. More preferably, $R^5$ is hydrogen or methyl, especially hydrogen.

Compounds of Formula I or II may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumicloracpentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus comprising application to the locus of a weed controlling amount of a compound or composition of the present invention. The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha, even more especially from 50 to 200 g/ha. The application is generally made by spraying the composition, typically by tractor mounted sprayer for large areas, but other methods such as dusting (for powders), drip or drench can also be used.

In certain circumstances, wherein a crop plant is tolerant of the compounds of the present invention (either inherently or via genetic engineering) the present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica*, Viola and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following schemes.

Scheme 1:- Reaction of an acid chloride with an aminotriazole or an aminotetrazole

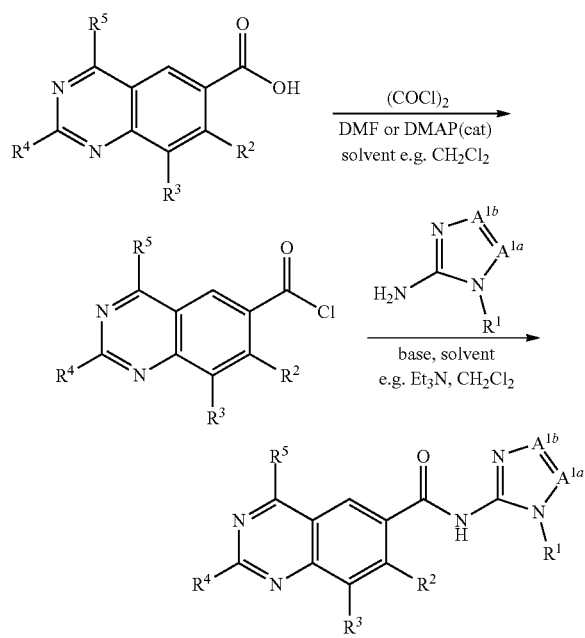

Scheme 2:- Reaction of an activated carboxylic acid with a 1-alkyl-5-aminotetrazole or an aminotriazole:

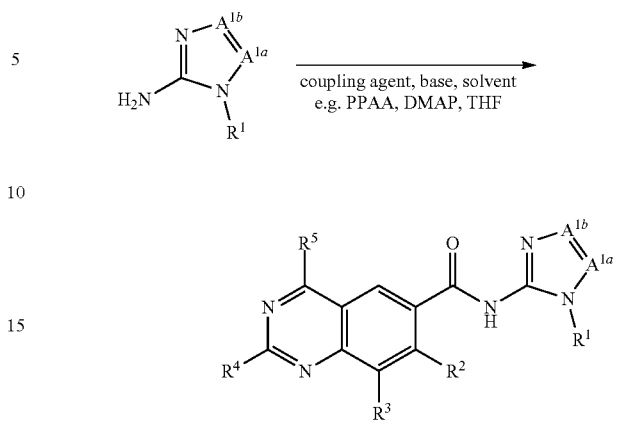

DMAP=4-(dimethylamino) pyridine, PPAA=1-propane-phosphonic acid cyclic anhydride, and the solvent is a non-protic organic solvent such as ethyl acetate, dichloromethane, tetrahydrofuran (THF) or toluene (PhMe).

Sheme 3: -Activation of an acid with N,N'-carbonyldiimidazole (CDI), and reaction with an aminotriazole or an aminotetrazole:

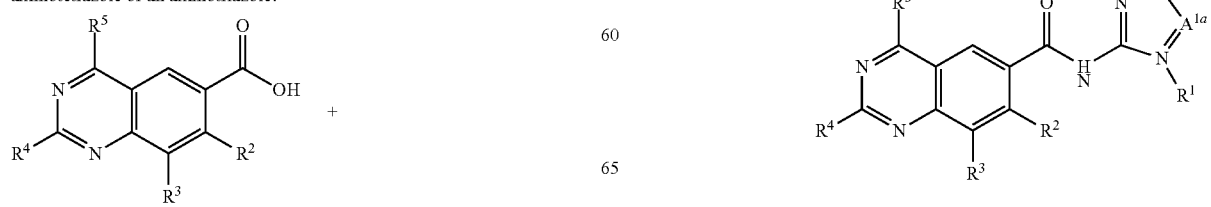

where THF=tetrahydrofuran and DBU=1,8-diazabicyclo[5.4.0]undec-7-ene

Scheme 4: Reaction of a carboxylic ester with an minotriazole or an aminotetrazole:

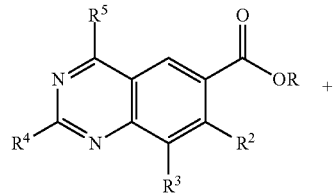

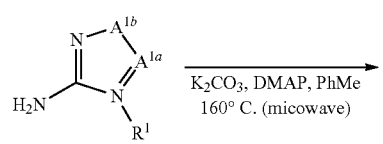

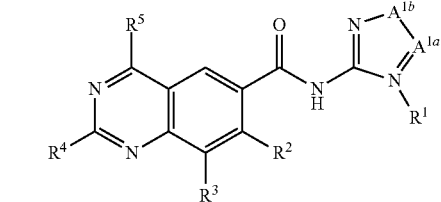

The carboxylic acids and esters can be prepared by known methods, or methods analogous to known methods. Examples of such methods are given below.

Scheme 5: -Preparation of carboxylic acids and esters

Where XPhos=2-Dicyclohexylphosphino-2',4',6'-triisopropylbiphenyl, XPhos Pd G3=(2-Dicyclohexylphosphino-2',4',6'-triisopropyl-1,1'-biphenyl)[2-(2'-amino-1,1'-biphenyl)]palladium(II) methanesulfonate, DIBAL=di-isobutyl-aluminium hydride and THF is tetrahydrofuran.

Scheme 6:- Preparation of carboxylic acids and esters

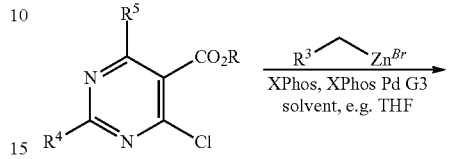

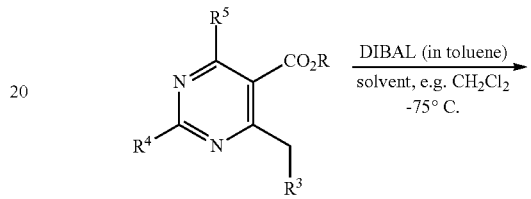

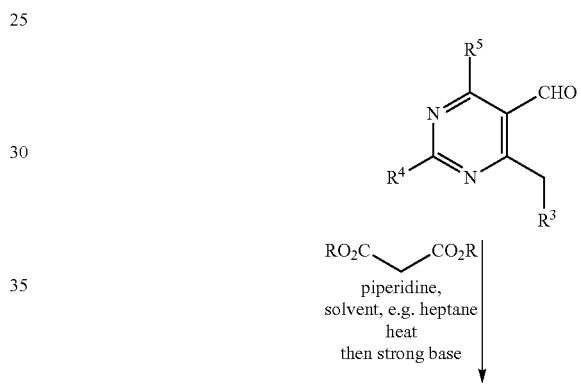

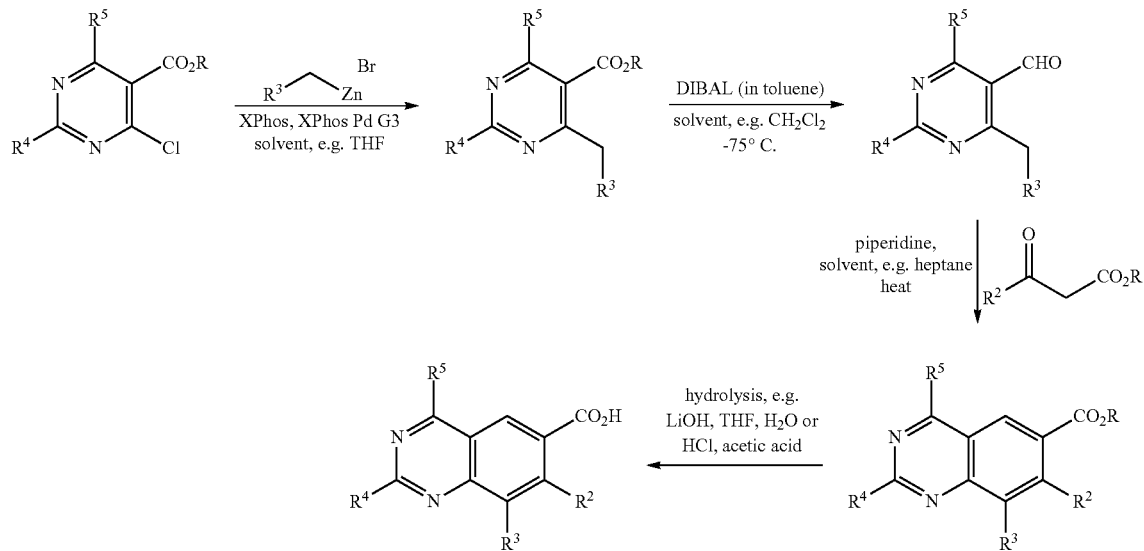

Where XPhos=2-Dicyclohexylphosphino-2',4',6'-triisopropylbiphenyl, XPhos Pd G3=(2-Dicyclohexylphosphino-2',4',6'-triisopropyl-1,1'-biphenyl)[2-(2'-amino-1,1'-biphenyl)]palladium(II) methanesulfonate, DIBAL=di-isobutylaluminium hydride and THF is tetrahydrofuran.

Scheme 7: Preparation of quinazoline carboxylic acids and esters

Where $R^2$ is halo or alkyl, $R^4$ is H, alkyl, cycloalkyl or haloalkyl, DMF is dimethylformamide, the optional base is, for example, sodium acetate and may be used when the amidine $R_4C(=NH)NH_2$ is added to the reaction as a salt such as its hydrochloride or acetate, Pd catalyst is, for example, [1,1'-bis(diphenylphosphino)-ferrocene]dichloropalladium(II)dichloro-methane adduct (Pd(dppf)Cl$_2$), S-Phos is 2-dicyclohexylphosphino-2',6'-dimethoxybiphenyl, DME is 1,2-dimethoxyethane and dioxane is 1,4-dioxane.

Scheme 8: Functional group conversion.

Where R is e.g alkyl-, haloalkyl-, alkoxyalkyl- and where X is a halogen or pseudohalogen. TMS=trimethylsilyl.

Scheme 9: Functional group conversion.

Where DMSO is dimethylsulfoxide.

Scheme 10: Functional group conversion.

17

-continued

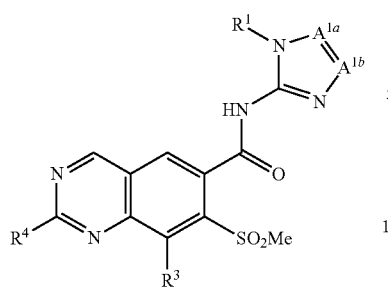

Where the oxidant is, for example, hydrogen peroxide, 3-chloroperbenzoic acid, sodium periodate, sodium hypochlorite or dimethyldioxirane.

The amino aldehyde starting materials utilised in Scheme 7 can be prepared by known methods, or methods analogous to known methods. Examples of such methods are given below.

Scheme 11: Preparation of amino aldehydes

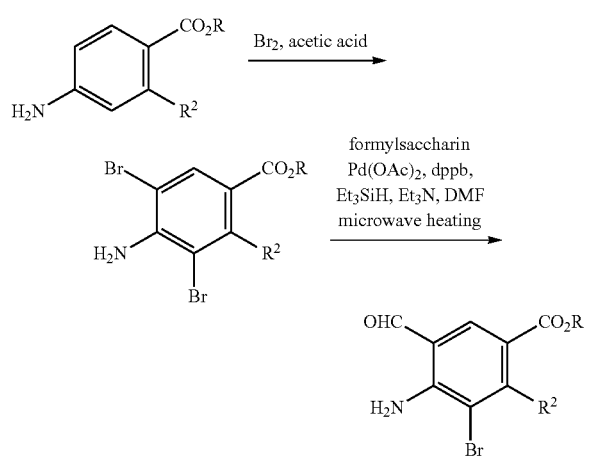

Where $R^2$ is, for example, an alkyl group, dppb is 1,4-butylenebis(diphenylphosphine) and DMF is dimethylformamide.

18

Scheme 12: Preparation of amino aldehydes

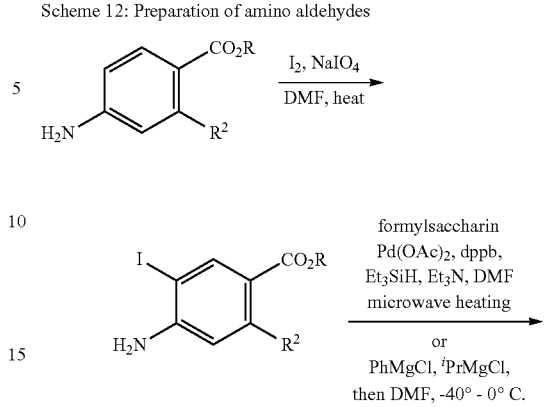

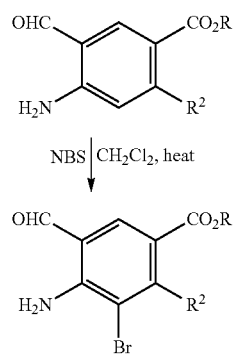

Where $R^2$ is, for example, halo, DMF is dimethylformamide, dppb is 1,4-butylenebis(diphenylphosphine) and NBS is N-bromosuccinimide.

The following non-limiting examples provide specific synthesis methods for representative compounds of the present invention, as referred to in Table 1 below.

EXAMPLE P1: PREPARATION OF COMPOUND 1.001

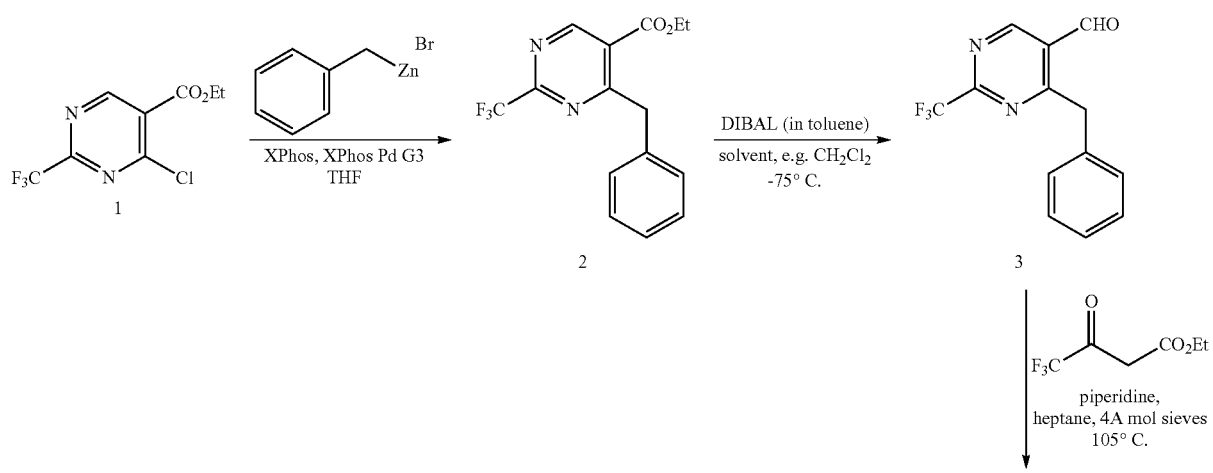

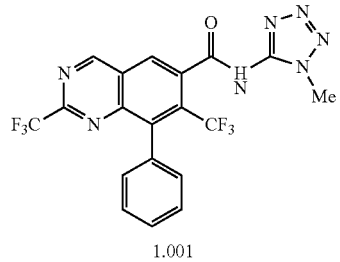

1.001

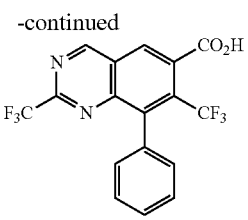

5

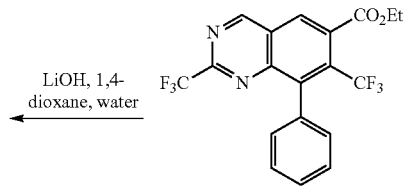

4

Step 1:

A stirred solution of compound 1 (1.00 g, 3.9279 mmol) in anhydrous degassed tetrahydrofuran (THF: 6 mL) was treated with XPHOS Pd G3 (0.2625 g, 0.29459 mmol) and XPHOS (0.14331 g, 0.29459 mmol) at room temperature. Benzylzinc bromide in THF (0.5 mol/L; 10.2 mL, 5.1062 mmol) was then added dropwise over 20 minutes via a syringe pump. The resulting dark orange/red solution was stirred at room temperature for 1 hour. The reaction mixture was then poured into dilute aqueous sodium potassium tartrate solution, and extracted with ethyl acetate (×3). The combined ethyl acetate extracts were washed with aqueous sodium potassium tartrate and brine, then passed through a phase-separating cartridge, and the filtrate was then evaporated under reduced pressure. The crude residue was purified by flash chromatography (0-7% ethyl acetate in hexane, 40 g silica) to afford compound 2 as a pale yellow oil.

1H NMR (400 MHz, CDCl3) δ 9.23 (s, 1H), 7.33-7.26 (m, 4H), 7.24-7.19 (m, 1H), 4.62 (s, 2H), 4.41 (q, 2H), 1.37 (t, 3H)

Step 2:

A stirred solution of compound 2 (0.893 g, 2.878 mmol) in anhydrous dichloromethane (15 mL) under a nitrogen atmosphere at −75° C. was treated dropwise with a solution of DIBAL in toluene (1.2 mol/L; 2.9 mL, 3.453 mmol) over 1 h via syringe pump at a rate such that the reaction temp stayed below −70 C. The resulting mixture was then stirred at −75° C. for 2 h, when GC-MS showed complete conversion. The reaction mixture was quenched with acetic acid (0.5 mL) in dichloromethane (0.5 mL), and was then allowed to warm to room temperature. The mixture was then washed with Rochelle's solution, 2M hydrochloric acid and brine, then passed through a phase-separating cartridge, and the filtrate was then evaporated under reduced pressure. The crude residue was purified by flash chromatography (0-20% ethyl acetate in hexanes, 40 g silica) to afford compound 3 as a pale yellow oil.

1H NMR (400 MHz, CDCl3) δ 10.37 (s, 1H), 9.18 (s, 1H), 7.32-7.28 (m, 4H), 7.28-7.22 (m, 1H), 4.62 (s, 2H)

Step 3:

A stirred solution of compound 3 (0.400 g, 1.503 mmol) in anhydrous heptane (16 mL) was treated with ethyl 4,4,4-trifluoro-3-oxo-butanoate (0.5533 g, 0.443 mL, 3.005 mmol) and piperidine (0.150 mL, 1.503 mmol), followed by activated powdered 4 A molecular sieves (1.00 g). The resulting mixture was heated at 105° C. (external temp) overnight under a nitrogen atmosphere. The reaction mixture was then cooled and diluted with ethyl acetate. The mixture was filtered through celite and the filtrate was washed with saturated aqueous sodium carbonate and brine, then passed through a phase-separating cartridge, and the filtrate was then evaporated under reduced pressure. The crude residue was purified by flash chromatography (0-25% ethyl acetate in hexanes, 24 g silica) to afford crude compound 4, which was used without further purification.

1H NMR (400 MHz, CDCl3) δ(inter alia) 9.70 (s, 1H), 8.33 (s, 1H), 7.60-7.45 (m, 3H), 7.35-7.30 (m, 2H), 4.48 (q, 2H), 1.43 (t, 3H)

Step 4:

A stirred solution of crude compound 4 (0.600 g, 1.45 mmol) in 1,4-dioxane (10 mL) at room temperature was treated with water (2.5 mL) and lithium hydroxide monohydrate (0.0694 g, 2.90 mmol). The resulting mixture was stirred at room temperature overnight, when LC-MS analysis indicated incomplete conversion. A further two equivalents of lithium hydroxide were added, and the reaction mixture was heated at 50° C. (external temp) for 3 hours, when LC-MS analysis showed complete consumption of compound 4. The reaction mixture was evaporated under reduced pressure, and the residue was dissolved in water (~15 mL). This was washed once with ethyl acetate. The aqueous phase was then acidified to pH1 with 2M hydrochloric acid, and the resulting mixture extracted with ethyl acetate. The ethyl acetate extract of the acidified solution was passed through a phase-separating cartridge, and the filtrate was evaporated under reduced pressure to afford crude compound 5, which was used without further purification.

1H NMR (400 MHz, CDCl3) δ 9.71 (s, 1H), 8.47 (s, 1H), 7.56-7.41 (m, 3H), 7.37-7.34 (m, 2H)

Step 5:

A stirred solution of compound 5 (0.180 g, 0.466 mmol) in anhydrous 1,4-dioxane (5 mL) at room temperature under a nitrogen atmosphere was treated with N,N'-carbonyldiimidazole (CDI: 0.091 g, 0.559 mmol), and the resulting mixture was heated to 100° C. (external temp) for 1 hour. A further 0.5 equivalents of CDI were added, and the mixture was heated for a further 1.5 hours. The mixture was allowed to cool to room temperature, then 5-amino-1-methyltetrazole (0.055 g, 0.559 mmol) was added in one portion, followed by 1,8-diazabibyblo[5.4.0]undec-7-ene (DBU: 0.071 mL, 0.466 mmol). The resulting mixture was heated to 100° C. for 90 min. A further 0.5 equivalent of 5-amino-1-methyltetrazole was then added and heating was continued for a further 1 hour. The reaction mixture was the cooled, concentrated under reduced pressure, poured into 2M HCl and extracted with ethyl acetate (×3). The ethyl acetate extracts were washed with brine, passed through a phase-separating cartridge, and the filtrate was evaporated under reduced pressure. The crude residue was then purified by chromatography to afford compound 1.001.

1H NMR (400 MHz, CD3OD) δ 9.92 (s, 1H), 8.75 (s, 1H), 7.52 (m, 3H), 7.39 (s, 2H), 4.13 (s, 3H)

EXAMPLE P2: PREPARATION OF COMPOUND 1.042

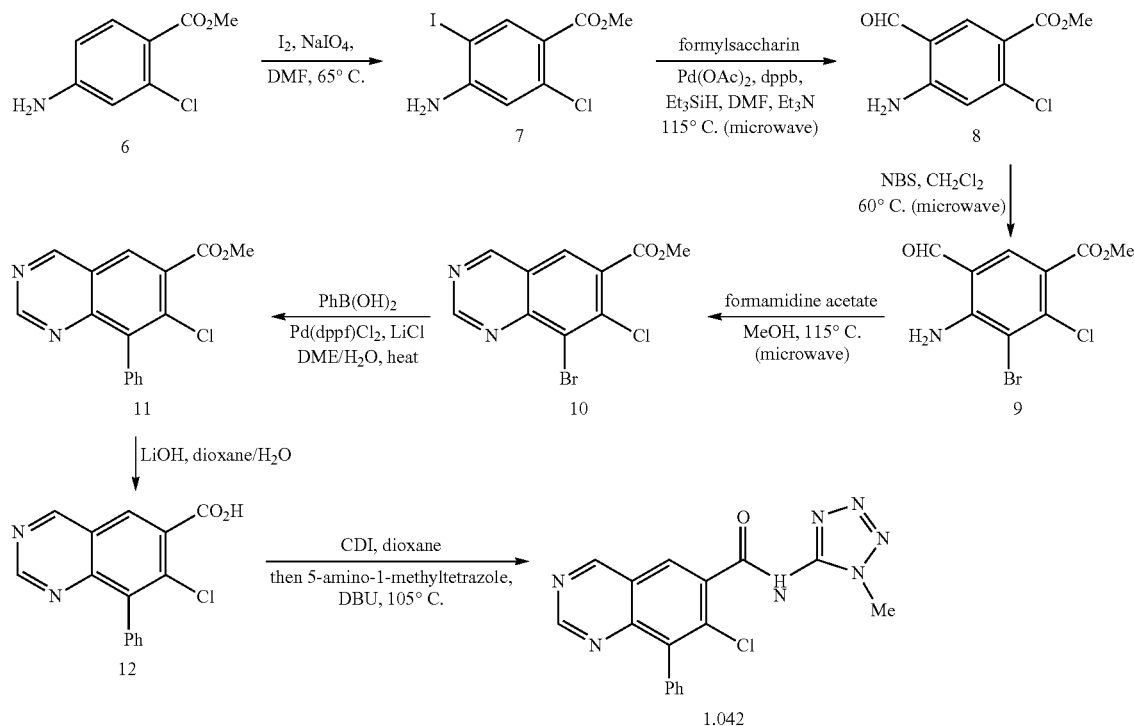

Step 1:

A stirred solution of compound 6 (5.00 g, 26.9 mmol) in N,N-dimethylformamide (DMF: 18.9 mL) was treated with sodium periodate (2.30 g, 10.8 mmol) and iodine (5.50 g, 21.6 mmol) at room temperature. The resulting brown solution was heated to 65° C. for 2 hours, and then allowed to cool to room temperature. The reaction mixture was then poured slowly into water (150 mL) with rapid stirring, and the resulting dark brown precipitate was collected by filtration (washing with water) and dried under suction. The resultant dark brown solid was added to 5% aqueous sodium metabisulfite solution with stirring, and the resulting suspension heated at 45-50° C. for 30 minutes. The brown solid was then collected by filtration (washing with water) and dried under suction. The solid was triturated with isopropanol (30 mL), with stirring, for 30 minutes, and was then filtered and dried under suction to afford compound 7 (5.86 g) as a brown solid.

1H NMR (400 MHz, CDCl3) δ 8.26 (s, 1H), 6.75 (s, 1H), 3.87 (s, 3H)

Step 2:

A mixture of compound 7 (0.500 g, 1.605 mmol), N-formylsaccharin (1.017 g, 4.815 mmol), palladium (II) acetate (0.036 g, 0.161 mmol) and 1,4-butylenebis(diphenylphosphine) (dppb; 0.140 g, 0.321 mmol) was treated with anhydrous N,N-dimethylformamide (3.210 mL) and triethylsilane (0.34 mL, 2.087 mmol) in a sealed 2-5 mL microwave vial under a nitrogen atmosphere at room temperature. The resulting mixture was stirred for 5 minutes, then stirring was stopped and triethylamine (0.671 mL, 4.815 mmol) was carefully layered over the reaction mixture [note: some effervescence]. The resulting mixture was stirred at room temperature for 1 min and then heated to 115° C. for 1 hour under microwave irradiation. The microwave vial was then carefully vented by piercing the septum with a needle, and the reaction mixture was poured into saturated aqueous sodium hydrogen carbonate solution. This mixture was extracted with ethyl acetate (3×), and the combined ethyl acetate extracts were washed with water (2×) and brine, then dried by passing through a phase-separating cartridge. The filtrate was evaporated under reduced pressure, and the crude residue was purified by flash chromatography (CombiFlash Rf, eluting with 0-20% ethylacetate in hexanes using a 12 g silica GOLD column) to afford compound 8 (0.165 g) as a pale yellow solid.

1H NMR (400 MHz, CDCl3) δ 9.86 (s, 1H), 8.22 (s, 1H), 6.73 (s, 1H), 3.90 (s, 3H)

Step 3:

A stirred solution of compound 8 (0.100 g, 0.468 mmol) in dichloromethane (5.0 mL) was treated with N-bromosuccinimide (NBS; 0.093 g, 0.515 mmol) at room temperature, and the resulting mixture was then heated at 60° C. for 1 hour under microwave irradiation. LC-MS analysis showed presence of a slight trace of compound 8 remaining, so a further 0.2 equivalents of N-bromosuccinimide were added and heating at 60° C. was continued for a further 30 minutes. The reaction mixture was cooled, washed with water, and then dried by passing through a phase-separating cartridge. The filtrate was evaporated under reduced pressure, and the crude residue was purified by flash chromatography (CombiFlash Rf, eluting with 0-20% ethyl acetate in hexanes using a 12 g silica column) to afford compound 9 as a yellow solid.

1H NMR (400 MHz, CDCl3) δ 9.84 (s, 1H), 8.19 (s, 1H), 3.92 (s, 3H)

Step 4:

A stirred suspension of compound 9 (0.110 g, 0.376 mmol) and formamidine acetate (0.141 mL, 1.504 mmol) in anhydrous methanol (5.0 mL) was heated at 150° C. for 1 h under microwave irradiation. The cooled reaction mixture was then evaporated under reduced pressure, diluted with ethyl acetate and washed with saturated aqueous sodium hydrogen carbonate solution. The ethyl acetate layer was dried by passing through a phase-separating cartridge, and the filtrate was then evaporated under reduced pressure. The crude residue was purified by flash chromatography (CombiFlash Rf, eluting with 0-50% ethyl acetate in hexanes using a 4 g silica column) to afford compound 10 as an off-white solid.

1H NMR (400 MHz, CDCl3) δ 9.54 (s, 1H), 9.45 (s, 1H), 8.35 (s, 1H), 4.04 (s, 3H)

Step 5:

A stirred solution of compound 10 (0.087 g, 0.289 mmol) in a degassed mixture of 1,2-dimethoxyethane (4.04 mL) and water (1.44 mL) was treated with sodium carbonate (0.153 g, 1.4427 mmol) bis(diphenylphosphino)ferrocene]-dichloropalladium(II) dichloromethane adduct (Pd(dppf) Cl$_2$; 0.024 g, 0.0289 mmol), lithium chloride (0.037 g, 0.866 mmol) and phenylboronic acid (0.0352 g, 0.289 mmol). The resulting mixture was heated under reflux under a nitrogen atmosphere for 2 hours. The reaction mixture was allowed to cool to room temperature, then concentrated under reduced pressure. The residue was poured into water and extracted with ethyl acetate (3×). The combined ethyl acetate extracts were washed with brine, dried by passing through a phase-separating cartridge, and the filtrate was then evaporated under reduced pressure. The crude residue was purified by flash chromatography (CombiFlash Rf, eluting with 0-40% ethyl acetate in hexanes using a 4 g silica GOLD column) to afford compound 11 (0.067 g) as a pale yellow oil.

1H NMR (400 MHz, CDCl3) δ 9.47 (s, 1H), 9.35 (s, 1H), 8.35 (s, 1H), 7.60-7.49 (m, 3H), 7.40-7.33 (m, 2H), 4.04 (s, 3H)

Step 6:

A stirred solution of compound 11 (0.063 g, 0.211 mmol) in 1,4-dioxane (1.0 mL) was treated with a solution of lithium hydroxide monohydrate (0.013 g, 0.316 mmol) in water (0.25 mL) at room temperature, and the resulting mixture was stirred overnight. The reaction mixture was evaporated under reduced pressure and the residue was dissolved in water (~2 mL) and acidified to pH ~5 with 2M hydrochloric acid. The resulting mixture was extracted (3×) with a 7:3 mixture of chloroform and isopropanol. The combined organic extracts were washed with brine and then dried by passing through a phase-separating cartridge. The filtrate was then evaporated under reduced pressure to afford compound 12 (0.060 g) as an off-white solid.

1H NMR (400 MHz, CDCl3/CD3OD) δ 9.48 (s, 1H), 9.32 (s, 1H), 8.45 (s, 1H), 7.63-7.47 (m, 3H), 7.42-7.33 (m, 2H)

Step 7:

A stirred solution of compound 12 (0.058 g, 0.204 mmol) in anhydrous 1,4-dioxane (3 mL) was treated with N,N'-carbonyldiimidazole (CDI; 0.050 g, 0.306 mmol) under a nitrogen atmosphere, and the resulting mixture was heated to 105° C. for 1 hour. 5-amino-1-methyltetrazole (0.030 g, 0.306 mmol) was then added, followed by 1,8-diazabicyclo [5.4.0]undec-7-ene (DBU; 0.0311 mL, 0.204 mmol), and the resulting mixture was heated at 105° C. for 90 minutes. The reaction mixture was allowed to cool to room temperature, and was then evaporated to dryness under reduced pressure. The crude residue was diluted with water and then acidified to pH 5 with 2M hydrochloric acid. The mixture was extracted (3×) with a 7:3 mixture of chloroform and isopropanol. The combined organic extracts were washed with brine, and dried by passing through a phase-separating cartridge. The filtrate was then evaporated under reduced pressure, and the crude residue was triturated with a mixture of hexane and dichloromethane to afford compound 1.042 (0.027 g) as an off-white solid.

1H NMR (400 MHz, CD3OD) δ 9.66 (s, 1H), 9.21 (s, 1H), 8.47 (s, 1H), 7.57-7.46 (m, 3H), 7.41-7.34 (m, 2H), 4.08 (s, 3H)

EXAMPLE P3: PREPARATION OF COMPOUND 1.048

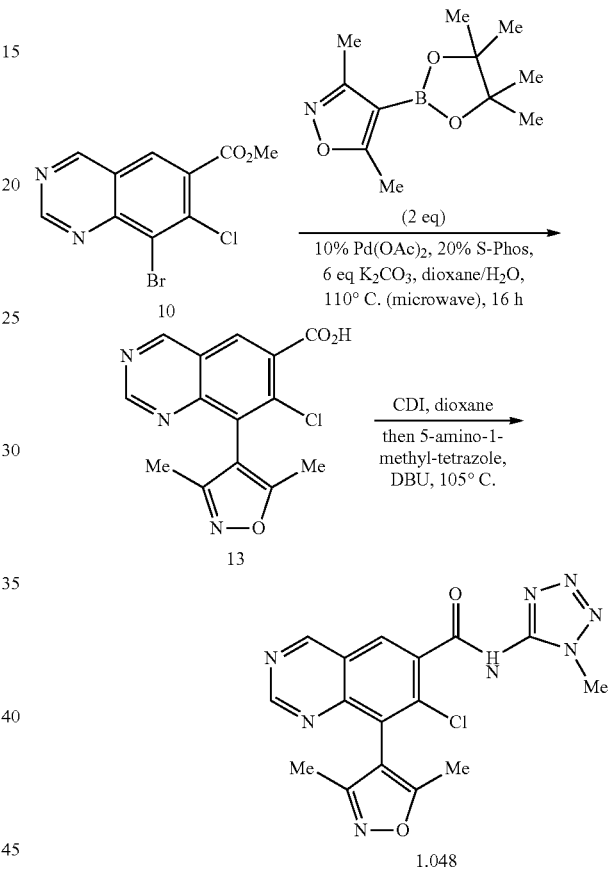

Step 1:

A stirred suspension of compound 10 (0.300 g, 0.995 mmol), 3,5-dimethyl-4-(4,4,5,5-tetramethyl-1,3,2-dioxaborolan-2-yl)isoxazole (0.444 g, 1.990 mmol), 2-dicyclohexylphosphino-2',6'-dimethoxybiphenyl (S-Phos: 0.092 g, 0.219 mmol), palladium (II) acetate (0.024 g, 0.010 mmol) and potassium carbonate (0.825 g, 5.970 mmol) in a degassed mixture of water (3 mL) and 1,4-dioxane (6 mL) was heated under reflux for 18 hours under a nitrogen atmosphere. The cooled reaction mixture was then concentrated under reduced pressure and diluted with water. This aqueous phase was washed with ethyl acetate, then acidified to pH 3 with 2M hydrochloric acid. The acidified mixture was then extracted with a 7:3 mixture of chloroform and isopropanol. The organic extracts were dried by passing through a phase-separating cartridge and evaporated under reduced pressure to afford crude compound 13 which was contaminated with pinacol (187 mg isolated). This crude product was used in the next step without further purification.

1H NMR (400 MHz, CD3OD) δ(inter alia) 9.56 (s, 1H), 9.19 (s, 1H), 8.48 (s, 1H), 2.13 (s, 3H), 1.95 (s, 3H)

Step 2:

By a method analogous to that described in Example P2, Step 7, but using crude compound 13 instead of compound 12 and purification of the crude product by reverse-phase chromatography (eluting with 15-100% water in acetonitrile containing 0.05% trifluoroacetic acid), compound 1.048 was obtained as an off-white solid.

1H NMR (400 MHz, d6-DMSO) δ 12.13 (s, 1H), 9.81 (s, 1H), 9.42 (s, 1H), 8.76 (s, 1H), 4.06 (s, 3H), 2.24 (s, 3H), 2.01 (s, 3H)

EXAMPLE P4: PREPARATION OF COMPOUND 1.006

Step 2:

By a method analogous to that described in Example P2, Step 2, but using compound 15 instead of compound 7, compound 16 was obtained as a pale yellow solid.

1H NMR (400 MHz, CDCl3) δ 9.81 (s, 1H), 8.17 (s, 1H), 3.89 (s, 3H), 2.79 (s, 3H)

Step 3:

By a method analogous to that described in Example P2, Step 4, but using compound 16 instead of compound 9 and 2,2,2-trifluoroacetamidine in place of formamidine acetate, compound 17 was obtained as an off-white solid.

1H NMR (400 MHz, CDCl3) δ 9.54 (s, 1H), 8.47 (s, 1H), 4.03 (s, 3H), 2.95 (s, 3H)

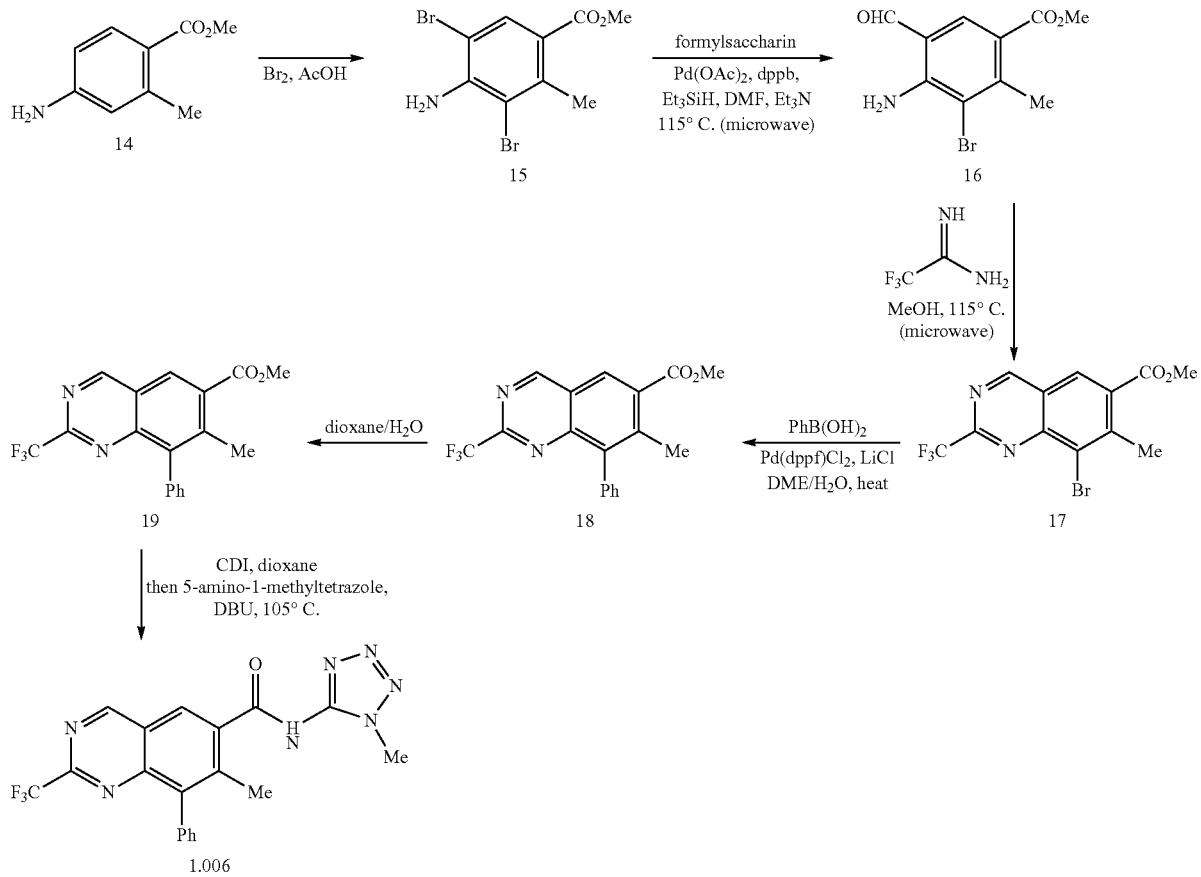

Step 1:

A stirred solution of compound 14 (1.0 g, 6.1 mmol) in acetic acid (10 mL) was treated dropwise with a solution of bromine (1.5 mL, 12 mmol) in acetic acid (5 mL). On completion of the addition, the resultant suspension was stirred at room temperature for 30 minutes, then water (50 mL) was added. A thick white ppt formed which was filtered, washed with water (3×50 mL) and air dried. The solid still contained water, so it was dissolved in dichloromethane and the solution was dried by passing through a hydrophobic frit. Evaporation of the solvent under reduced pressure afforded compound 15 as a cream solid (1.90 g).

1H NMR (400 MHz, CDCl3) δ 8.02 (s, 1H), 6.23 (br. s., 2H), 3.85 (s, 3H), 2.67 (s, 3H)

Step 4:

By a method analogous to that described in Example P2, Step 5, but using compound 17 instead of compound 10, compound 18 was obtained as a white solid.

1H NMR (400 MHz, CDCl3) δ 9.55 (s, 1H), 8.52 (s, 1H), 7.55-7.44 (m, 3H), 7.29-7.26 (m, 2H), 4.03 (s, 3H), 2.57 (s, 3H)

Step 5:

By a method analogous to that described in Example P2, Step 6, but using compound 18 instead of compound 11, compound 19 was obtained as an off-white solid.

1H NMR (400 MHz, CDCl3) δ 9.62 (s, 1H), 8.76 (s, 1H), 7.59-7.44 (m, 3H), 7.31-7.25 (m, 2H), 2.66 (s, 3H)

Step 6:

By a method analogous to that described in Example P2, Step 7, but using compound 19 instead of compound 12, compound 1.006 was obtained as a pale yellow solid.

1H NMR (400 MHz, CDCl3) δ 11.78 (s, 1H), 9.73 (s, 1H), 8.68 (s, 1H), 7.58-7.43 (m, 3H), 7.32-7.30 (m, 2H), 4.19 (s, 3H), 2.56 (s, 3H)

EXAMPLE P5: PREPARATION OF COMPOUND 1.045

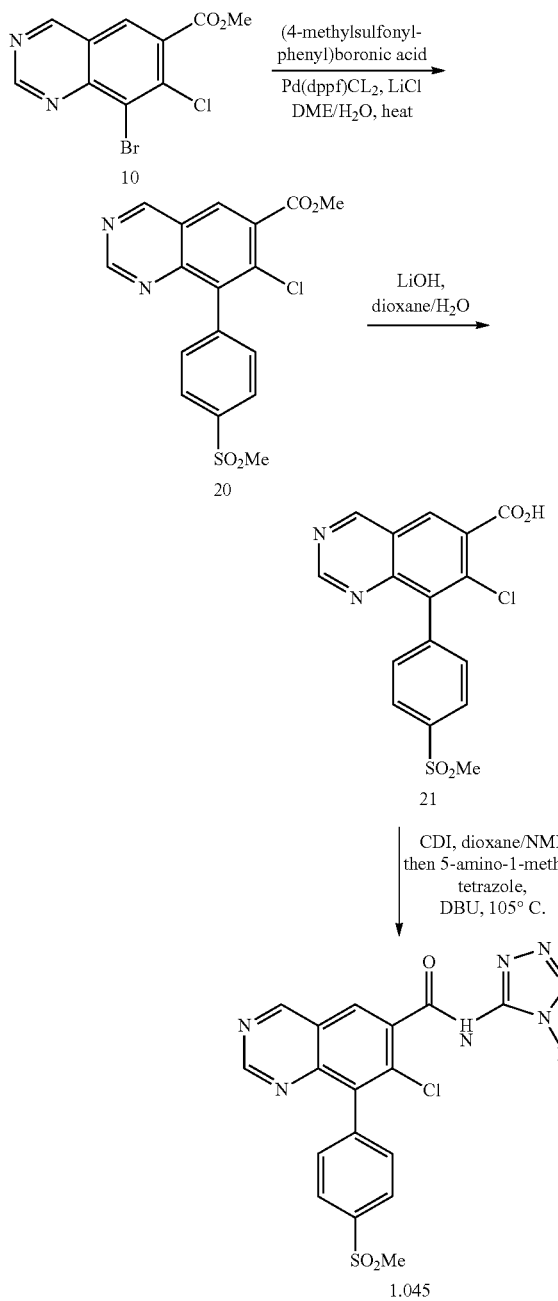

1H NMR (400 MHz, CD3OD) δ 9.68 (s, 1H), 9.23 (s, 1H), 8.65 (s, 1H), 8.17-8.11 (m, 2H), 7.70-7.63 (m, 2H), 4.04 (s, 3H), 3.25 (s, 3H)

Step 2:

By a method analogous to that described in Example P2, Step 6, but using compound 20 instead of compound 11, compound 21 was obtained as a dark solid.

1H NMR (400 MHz, CD3OD) δ 9.67 (s, 1H), 9.21 (s, 1H), 8.60 (s, 1H), 8.16-8.12 (m, 2H), 7.71-7.64 (m, 2H), 3.25 (s, 3H)

Step 3:

By a method analogous to that described in Example P2, Step 7, but using compound 21 instead of compound 12, a mixture of 1,4-dioxane and N-methylpyrrolidone as solvent, and purification of the crude product by reverse-phase chromatography (eluting with 15-100% water in acetonitrile containing 0.05% trifluoroacetic acid), compound 1.045 was obtained as an off-white solid.

1H NMR (400 MHz, d6-DMSO) δ12.13 (s, 1H), 9.82 (s, 1H), 9.36 (s, 1H), 8.77 (s, 1H), 8.12 (d, 2H), 7.70 (d, 2H), 4.06 (s, 3H), 3.37 (s, 3H)

EXAMPLE P6: PREPARATION OF COMPOUND 1.071

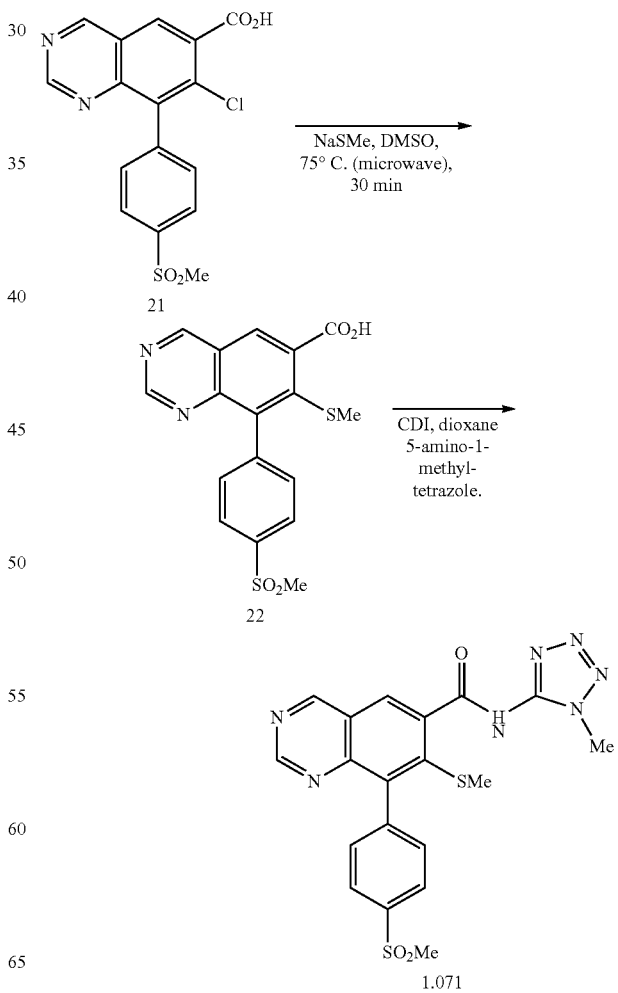

Step 1:

By a method analogous to that described in Example P2, Step 5, but using (4-methylsulfonylphenyl)boronic acid instead of phenylboronic acid, compound 20 was obtained as a pale yellow solid.

Step 1:

A stirred solution of compound 21 (0.100 g, 0.276 mmol) in anhydrous dimethylsulfoxide (5 mL) was treated with sodium thiomethoxide (0.102 g, 1.378 mmol). The resulting mixture was heated at 75° C. for 30 minutes under microwave irradiation. The reaction mixture was then poured into water (~40 mL) and acidified to pH 3 with 2M hydrochloric acid. This mixture was extracted with a 7:3 mixture of chloroform and isopropanol (3×15 mL). The combined organic extracts were dried by passing through a phase-separating cartridge, and the filtrate was evaporated under reduced pressure. The residue was purified by reverse-phase chromatography (eluting with 15-100% water in acetonitrile containing 0.05% trifluoroacetic acid) to afford compound 22 as a yellow gum.

m/z 375.09 [M+H]+, 393.08 [M(hydrate)+H]+

Step 2:

By a method analogous to that described in Example P2, Step 7, but using compound 22 instead of compound 12, and purification of the crude product by reverse-phase chromatography (eluting with 15-100% water in acetonitrile containing 0.05% trifluoroacetic acid), compound 1.071 was obtained as an off-white solid.

1H NMR (400 MHz, d6-DMSO) δ 11.97 (s, 1H), 9.77 (s, 1H), 9.32 (s, 1H), 8.61 (s, 1H), 8.09-8.07 (m, 2H), 7.72-7.68 (m, 2H), 4.09 (s, 3H), 3.36 (s, 3H), 2.14 (s, 3H)

TABLE 1

Examples of herbicidal compounds of the present invention.

(I)

| CMP | $R^1$ | $R^2$ | $R^3$ | $R^4$ | $A^{1a}$ | $A^{1b}$ | NMR |
|---|---|---|---|---|---|---|---|
| 1.001 | Me | $CF_3$ | Phenyl- | $CF_3$ | N | N | (400 MHz, CD3OD) δ 9.92 (s, 1H), 8.75 (s, 1H), 7.52 (m, 3H), 7.39 (s, 2H), 4.13 (s, 3H) |
| 1.002 | Me | $CF_3$ | Phenyl- | H | N | N | |
| 1.003 | Me | $CF_3$ | Phenyl- | Me | N | N | |
| 1.004 | Me | Me | Phenyl- | H | N | N | |
| 1.005 | Me | Me | Phenyl- | Me | N | N | |
| 1.006 | Me | Me | Phenyl- | $CF_3$ | N | N | 1H NMR (400 MHz, CDCl3) δ 11.78 (s, 1H), 9.73 (s, 1H), 8.68 (s, 1H), 7.58-7.43 (m, 3H), 7.32-7.30 (m, 2H), 4.19 (s, 3H), 2.56 (s, 3H) |
| 1.007 | Me | $CF_3$ | 4-MeS(O)$_2$-phenyl- | $CF_3$ | N | N | |
| 1.008 | Me | $CF_3$ | 4-MeO-phenyl- | $CF_3$ | N | N | |
| 1.009 | Me | $CF_3$ | 3-Cl-phenyl- | $CF_3$ | N | N | |
| 1.010 | Me | $CF_3$ | 3-Me-phenyl- | $CF_3$ | N | N | |
| 1.011 | Me | $CF_3$ | 3-CF3-phenyl- | Me | N | N | |
| 1.012 | Me | $CF_3$ | 2-F-phenyl | Me | N | N | |
| 1.013 | Et | $CF_3$ | Phenyl- | $CF_3$ | N | N | |
| 1.014 | nPr | $CF_3$ | Phenyl- | $CF_3$ | N | N | |
| 1.015 | Me | Me | 4-MeO-phenyl- | $CF_3$ | N | N | |
| 1.016 | Me | Me | 4-MeS-phenyl- | $CF_3$ | N | N | |
| 1.017 | Me | Me | 4-MeS(O)$_2$-phenyl- | $CF_3$ | N | N | |
| 1.018 | Me | Me | 4-F-phenyl- | $CF_3$ | N | N | |
| 1.019 | Me | Me | 2-MeOpyrimidin-5-yl | $CF_3$ | N | N | |
| 1.020 | Me | Cl | 3,5-dimethylisoxazol-4-yl- | $CF_3$ | N | N | |
| 1.021 | Me | Cl | Phenyl- | $CF_3$ | N | N | 1H NMR (400 MHz, CDCl3 δ 9.69 (s, 3H), 8.50 (s, 1H), 7.61-7.49 (m, 3H), 7.44-7.42 (m, 2H), 4.19 (s, 3H) |
| 1.022 | Me | Cl | 4-MeO-phenyl- | $CF_3$ | N | N | |
| 1.023 | Me | Cl | 4-MeS-phenyl- | $CF_3$ | N | N | |
| 1.024 | Me | Cl | 4-MeS(O)$_2$-phenyl- | $CF_3$ | N | N | |
| 1.025 | Me | Cl | 4-F-phenyl- | $CF_3$ | N | N | |
| 1.026 | Me | Cl | 2-MeO-pyrimidin-5-yl- | $CF_3$ | N | N | |
| 1.027 | Me | Cl | 3,5-dimethylisoxazol-4-yl- | $CF_3$ | N | N | |
| 1.028 | Me | Cl | Phenyl- | c-Pr | N | N | 1H NMR (400 MHz, CDCl3) δ 11.06 (s, 1H), 9.34 (s, 1H), 8.32 (s, 1H), 7.56-7.45 (m, 3H), 7.43-7.37 (m, 2H), 4.16 (s, 3H), 2.36-2.25 (m, 1H), 1.16-1.03 (m, 4H) |

TABLE 1-continued

Examples of herbicidal compounds of the present invention.

| CMP | R¹ | R² | R³ | R⁴ | A^{1a} | A^{1b} | NMR |
|---|---|---|---|---|---|---|---|
| 1.029 | Me | Cl | 4-MeO-phenyl- | c-Pr | N | N | |
| 1.030 | Me | Cl | 4-MeS-phenyl- | c-Pr | N | N | |
| 1.031 | Me | Cl | 4-MeS(O)₂-phenyl- | c-Pr | N | N | |
| 1.032 | Me | Cl | 4-F-phenyl- | c-Pr | N | N | |
| 1.033 | Me | Cl | 2-MeO-pyrimidin-5-yl- | c-Pr | N | N | |
| 1.034 | Me | Cl | 3,5-dimethylisoxazol-4-yl- | c-Pr | N | N | |
| 1.035 | Me | Cl | Phenyl- | i-Pr | N | N | 1H NMR (400 MHz, CD3OD) δ 9.57 (s, 1H), 8.43 (s, 1H), 7.55-7.46 (m, 3H), 7.42-7.37 (m, 2H), 4.12 (s, 3H), 3.23 (m, 1H), 1.26 (d, 6H) |
| 1.036 | Me | Cl | 4-MeO-phenyl- | i-Pr | N | N | |
| 1.037 | Me | Cl | 4-MeS-phenyl- | i-Pr | N | N | |
| 1.038 | Me | Cl | 4-MeS(O)₂-phenyl- | i-Pr | N | N | |
| 1.039 | Me | Cl | 4-F-phenyl- | i-Pr | N | N | |
| 1.040 | Me | Cl | 3,5-dimethylisoxazol-4-yl- | i-Pr | N | N | |
| 1.041 | Me | Cl | 2-MeO-pyrimidin-5-yl- | i-Pr | N | N | |
| 1.042 | Me | Cl | Phenyl- | H | N | N | 1H NMR (400 MHz, CD3OD) δ 9.66 (s, 1H), 9.21 (s, 1H), 8.47 (s, 1H), 7.57-7.46 (m, 3H), 7.41-7.34 (m, 2H), 4.08 (s, 3H) |
| 1.043 | Me | Cl | 4-MeO-phenyl- | H | N | N | 1H NMR (400 MHz, CD3OD) δ 9.67 (s, 1H), 9.26 (s, 1H), 8.50 (s, 1H), 7.35-7.33 (m, 2H), 7.17-7.05 (m, 2H), 4.14 (s, 3H), 3.91 (s, 3H) |
| 1.044 | Me | Cl | 4-MeS-phenyl- | H | N | N | 1H NMR (400 MHz, CD3OD) d 9.66 (s, 1H), 9.24 (s, 1H), 8.50 (s, 1H), 7.46 ? 7.40 (m, 2H), 7.33-7.31 (m, 2H), 4.12 (s, 3H), 2.56 (s, 3H) |
| 1.045 | Me | Cl | 4-MeS(O)₂-phenyl- | H | N | N | 1H NMR (400 MHz, d6-DMSO) δ 12.13 (s, 1H), 9.82 (s, 1H), 9.36 (s, 1H), 8.77 (s, 1H), 8.12 (d, 2H), 7.70 (d, 2H), 4.06 (s, 3H), 3.37 (s, 3H) |
| 1.046 | Me | Cl | 4-F-phenyl- | H | N | N | 1H NMR (400 MHz, CD3OD) d 9.69 (s, 1H), 9.27 (s, 1H), 8.55 (s, 1H), 7.50-7.39 (m, 2H), 7.32-7.28 (m, 2H), 4.14 (s, 3H) |
| 1.047 | Me | Cl | 2-MeO-pyrimidin-5- | H | N | N | 1H NMR (400 MHz, CD3OD) d 9.70 (s, 1H), 9.32 (s, 1H), 8.71 (s, 2H), 8.60 (s, 1H), 4.13 (s, 6H) |
| 1.048 | Me | Cl | 3,5-dimethylisoxazol-4-yl- | H | N | N | 1H NMR (400 MHz, d6-DMSO) δ 12.13 (s, 1H), 9.81 (s, 1H), 9.42 (s, 1H), 8.76 (s, 1H), 4.06 (s, 3H), 2.24 (s, 3H), 2.01 (s, 3H) |
| 1.049 | Et | CF₃ | Phenyl- | CF₃ | N | N | |
| 1.050 | n-Pr | CF₃ | Phenyl- | CF₃ | N | N | |
| 1.051 | n-Bu | CF₃ | Phenyl- | CF₃ | N | N | |
| 1.052 | n-Bu | Me | Phenyl- | CF₃ | N | N | |
| 1.053 | n-Pr | Me | Phenyl- | CF₃ | N | N | |
| 1.054 | Et | Me | Phenyl- | CF₃ | N | N | |
| 1.055 | Et | Cl | Phenyl- | CF₃ | N | N | |
| 1.056 | n-Pr | Cl | Phenyl- | CF₃ | N | N | |
| 1.057 | n-Bu | Cl | Phenyl- | CF₃ | N | N | |
| 1.058 | n-Bu | Cl | Phenyl- | c-Pr | N | N | |
| 1.059 | n-Pr | Cl | Phenyl- | c-Pr | N | N | |

TABLE 1-continued

Examples of herbicidal compounds of the present invention.

(I)

| CMP | R¹ | R² | R³ | R⁴ | A$^{1a}$ | A$^{1b}$ | NMR |
|---|---|---|---|---|---|---|---|
| 1.060 | Et | Cl | Phenyl- | c-Pr | N | N | |
| 1.061 | Et | Cl | Phenyl- | i-Pr | N | N | |
| 1.062 | n-Pr | Cl | Phenyl- | i-Pr | N | N | |
| 1.063 | n-Bu | Cl | Phenyl- | i-Pr | N | N | |
| 1.064 | n-Bu | Cl | Phenyl- | H | N | N | |
| 1.065 | n-Pr | Cl | Phenyl- | H | N | N | |
| 1.066 | Et | Cl | Phenyl- | H | N | N | |
| 1.067 | n-Pr | Cl | 4-MeS(O)$_2$-phenyl- | H | N | N | |
| 1.068 | n-Pr | Cl | 3,5-dimethylisoxazol-4-yl- | H | N | N | 1H NMR (400 MHz, d6-DMSO) δ 12.03 (s, 1H), 9.83 (s, 1H), 9.42 (s, 1H), 8.75 (s, 1H), 4.37 (t, 2H), 2.24 (s, 3H), 2.01 (s, 3H), 1.96 - 1.90 (m, 2H), 0.91 (t, 3H) |
| 1.069 | Me | Cl | Phenyl- | CF$_3$ | N | CH | |
| 1.070 | Me | Cl | Phenyl- | CF$_3$ | CH | N | |
| 1.071 | Me | MeS- | 4-MeS(O)$_2$-phenyl- | H | N | N | 1H NMR (400 MHz, d6-DMSO) δ 11.97 (s, 1H), 9.77 (s, 1H), 9.32 (s, 1H), 8.61 (s, 1H), 8.09-8.07 (m, 2H), 7.72-7.68 (m, 2H), 4.09 (s, 3H), 3.36 (s, 3H), 2.14 (s, 3H) |
| 1.072 | Me | MeS(O)- | 4-MeS(O)$_2$-phenyl- | H | N | N | |
| 1.073 | Me | MeS(O)$_2$- | 4-MeS(O)$_2$-phenyl- | H | N | N | |
| 1.074 | Me | Cl | 2-Me-phenyl- | H | N | N | |

BIOLOGICAL EXAMPLES

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 500 g/h unless otherwise stated. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

| | POST Application | | | | | | PRE Application | | | | | |
|---|---|---|---|---|---|---|---|---|---|---|---|---|
| Compound | LOLPE | SOLNI | AMARE | SETFA | ECHCG | IPOHE | LOLPE | SOLNI | AMARE | SETFA | ECHCG | IPOHE |
| 1.001* | 4 | 5 | 5 | 5 | 5 | 5 | 1 | 5 | 5 | 3 | 5 | 4 |
| 1.006 | NT | NT | 5 | 5 | 5 | 5 | NT | NT | 5 | 5 | 2 | 3 |
| 1.021 | NT | NT | 5 | 5 | 5 | 5 | NT | NT | 5 | 5 | 5 | 5 |
| 1.028 | NT | NT | 5 | 5 | 5 | 5 | NT | NT | 5 | 5 | 5 | 3 |
| 1.035 | NT | NT | 5 | 5 | 5 | 5 | NT | NT | 5 | 5 | 5 | 4 |
| 1.042 | NT | NT | 5 | 5 | 5 | 5 | NT | NT | 5 | 5 | 5 | 5 |

*Applied at 250 g/ha.
NT = not tested.

The invention claimed is:

1. A compound of Formula (I):

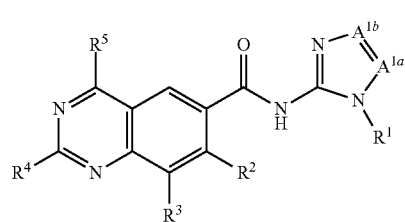

or an agronomically acceptable salt thereof, wherein:

$A^{1a}$ and $A_{1b}$ are independently selected from CH and N, wherein $A^{1a}$ and $A^{1b}$ are not both CH;

$R^1$ is selected from the group consisting of $C_1$-$C_6$-alkyl-, $C_1$-$C_6$-alkoxy$C_1$-$C_3$-alkyl-, $C_1$-$C_6$haloalkoxy$C_1$-$C_3$alkyl-, $C_1$-$C_6$haloalkyl-, $C_2$-$C_6$alkenyl-, $C_2$-$C_6$-haloalkenyl-, $C_2$-$C_6$alkynyl-, $C_2$-$C_6$haloalkynyl-, heteroaryl-, ($C_3$-$C_7$)-cycloalkyl-, heterocyclyl- and phenyl-, wherein the heteroaryl-, ($C_3$-$C_7$)-cycloalkyl-, heterocyclyl- and phenyl- are optionally substituted by one or more substituents selected from the group consisting of halogen, nitro, cyano, $C_1$-$C_6$alkyl-, $C_1$-$C_6$haloalkyl-, $C_3$-$C_6$cycloalkyl-, $C_1$-$C_6$alkyl-S(O)p-, $C_1$-$C_3$alkoxy- and $C_1$-$C_6$alkoxy$C_1$-$C_4$alkyl-;

$R^2$ is selected form the group consisting of $C_1$-$C_6$alkyl-, $C_1$-$C_6$alkoxy-, $C_1$-$C_6$ haloalkyl-, $C_1$-$C_6$haloalkoxy-, $C_1$-$C_6$alkoxy$C_1$-$C_6$alkyl-, $C_1$-$C_3$alkoxy$C_2$-$C_3$alkoxy$C_1$-$C_3$alkyl-, $C_1$-$C_3$alkoxy$C_1$-$C_3$-haloalkyl-, $C_1$-$C_3$-alkoxy$C_1$-$C_3$-alkoxy$C_2$-$C_3$haloalkyl-, halogen, cyano, nitro, $C_1$-$C_6$alkyl-S(O)p-, $C_1$-$C_6$haloalkyl-S(O)p-, $C_4$-$C_6$oxasubstituted-cycloalkoxy$C_1$-$C_3$alkyl-, $C_4$-$C_6$-oxasubstituted-cycloalkoxy-$C_1$-$C_3$haloalkyl-, ($C_1$-$C_3$alkanesulfonyl-$C_1$-$C_3$ alkylamino)-$C_1$-$C_3$alkyl- and ($C_1$-$C_3$alkanesulfonyl-$C_3$-$C_4$cycloalkylamino)-$C_1$-$C_3$alkyl-;

$R^3$ is aryl or a 5 or 6-membered heteroaryl, the heteroaryl containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxy$C_1$-$C_3$alkyl-, $C_1$-$C_6$alkoxy$C_1$-$C_3$alkoxy-, $C_1$-$C_6$haloalkoxy-, $C_1$-$C_6$alkyl-S(O)p-, —$NR^{6a}R^{6b}$, cyano and nitro;

$R^4$ is selected from the group consisting of hydrogen, halogen, $C_1$-$C_6$alkyl-, $C_3$-$C_6$cycloalkyl-, $C_1$-$C_6$alkoxy-$C_1$-$C_3$alkyl-, $C_1$-$C_6$-haloalkoxy$C_1$-$C_3$-alkyl-, $C_1$-$C_6$haloalkyl-, $C_2$-$C_6$alkenyl-, $C_2$-$C_6$haloalkenyl-, $C_2$-$C_6$alkynyl-, $C_2$-$C_6$haloalkynyl-, $C_1$-$C_6$alkoxy-, $C_1$-$C_6$alkyl-S(O)p- and $NR^{6a}R^{6b}$;

$R^5$ is selected from the group consisting of hydrogen, halogen and $C_1$-$C_6$alkyl-;

$R^{6a}$ and $R^{6b}$ are independently selected from the group consisting of hydrogen and $C_1$-$C_6$alkyl or together form a $C_4$-$C_6$ alkylene chain; and p=0, 1 or 2.

2. The compound according to claim 1, wherein $A^{1a}$ and $A^{1b}$ are N.

3. The compound of claim 1, wherein $R^1$ is selected from the group consisting of methyl, ethyl and n-propyl.

4. The compound according to claim 1, wherein $R^2$ is selected form the group consisting of $C_1$-$C_6$alkyl-, $C_1$-$C_6$alkoxy-, $C_1$-$C_6$ haloalkyl-, halogen and $C_1$-$C_6$alkyl-S(O)$_p$—.

5. The compound according to claim 1, wherein $R^3$ is an aryl or heteroaryl selected from the group consisting of phenyl, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl.

6. The compound according to claim 5, wherein $R^3$ is selected from the group consisting of phenyl, isoxazolyl and pyrimidinyl.

7. The compound according to claim 1, wherein $R^4$ is selected from the group consisting of hydrogen, $C_1$-$C_6$alkyl- and $C_1$-$C_6$haloalkyl-.

8. The compound according to claim 7, wherein $R^4$ is selected from the group consisting of hydrogen, methyl and trifluoromethyl.

9. The compound according to claim 1, wherein $R^5$ is hydrogen.

10. A herbicidal composition comprising the compound of formula 1 according to claim 1 and an agriculturally acceptable formulation adjuvant.

11. The herbicidal composition according to claim 10, further comprising at least one additional pesticide.

12. The herbicidal composition according to claim 11, wherein the additional pesticide is a herbicide or herbicide safener.

13. A method of controlling weeds at a locus comprising applying to the locus of a weed, a weed controlling amount of the compound according to claim 1.

* * * * *